(12) United States Patent  (10) Patent No.: US 7,766,811 B2
Haverich                    (45) Date of Patent:     *Aug. 3, 2010

(54) METHODS AND DEVICES FOR IMPROVING CARDIAC OUTPUT

(75) Inventor: Axel Haverich, Isernhagen (DE)

(73) Assignee: corLife GbR, Hannover (DE)

( * ) Notice: Subject to any disclaimer, the term of this patent is extended or adjusted under 35 U.S.C. 154(b) by 492 days.

This patent is subject to a terminal disclaimer.

(21) Appl. No.: 10/545,993

(22) PCT Filed: Feb. 18, 2004

(86) PCT No.: PCT/IB2004/000853

§ 371 (c)(1),
(2), (4) Date: May 31, 2006

(87) PCT Pub. No.: WO2004/073555

PCT Pub. Date: Sep. 2, 2004

(65) Prior Publication Data

US 2006/0241544 A1    Oct. 26, 2006

(51) Int. Cl.
A61N 1/362 (2006.01)
(52) U.S. Cl. .................................................. 600/16
(58) Field of Classification Search ............ 600/16, 600/17, 18; 623/3.14, 1.1, 1.36, 1.49
See application file for complete search history.

(56) References Cited

U.S. PATENT DOCUMENTS

| 4,769,031 | A |   | 9/1988  | McGough et al. |
| 4,957,504 | A | * | 9/1990  | Chardack ............... 623/3.14 |
| 5,290,227 | A | * | 3/1994  | Pasque ................... 600/16 |
| 5,429,144 | A |   | 7/1995  | Wilk |
| 5,984,956 | A |   | 11/1999 | Tweden et al. |
| 6,001,056 | A |   | 12/1999 | Jassawalla et al. |
| 6,302,892 | B1 |  | 10/2001 | Wilk |
| 7,238,151 | B2 | * | 7/2007 | Frazier ................... 600/16 |
| 2001/0025634 | A1 | | 10/2001 | Poggio et al. |
| 2004/0116769 | A1 | * | 6/2004 | Jassawalla et al. ........ 600/16 |

FOREIGN PATENT DOCUMENTS

| JP | 2-114969     | 4/1990  |
| JP | 2002-502663 A | 1/2002 |
| JP | 2003-530916 A | 10/2003 |

(Continued)

OTHER PUBLICATIONS

Cooley, et al., "Apicoaortic Conduit for Left Ventricular Outflow Tract Obstruction: Revisited," (2000) *The Society for Thoracic Surgeons*, 69:1511-1514.

(Continued)

*Primary Examiner*—George Manuel
(74) *Attorney, Agent, or Firm*—Venable, LLP; Ann S. Hobbs

(57) ABSTRACT

Methods and devices are provided for improving cardiac output. The methods involve establishing a fluid communication pathway between the left ventricle and another natural or prosthetic structure. In one method, a conduit is implanted between the left ventricle and the descending aorta where ventricular blood flows from the left ventricle directly into the descending aorta and bypassing the aortic valve. The devices include such conduits and valves for forming the fluid communication pathways.

11 Claims, 8 Drawing Sheets

FOREIGN PATENT DOCUMENTS

| | | |
|---|---|---|
| WO | WO 97/27897 | 8/1997 |
| WO | WO 97/27898 | 8/1997 |
| WO | WO-99/40868 | 8/1999 |
| WO | WO-01/17440 A1 | 3/2001 |
| WO | WO-01/78801 A2 | 10/2001 |

OTHER PUBLICATIONS

Notice of Reasons for Rejection Issued May 27, 2009 in Japanese Patent Application No. 2006-502492.

* cited by examiner

METHODS AND DEVICES FOR IMPROVING CARDIAC OUTPUT

FIELD OF THE INVENTION

The present invention is directed to improving cardiac output. More particularly, the invention relates to devices and methods for establishing a blood flow conduit from the left ventricle of the heart to the aorta to improve cardiac output.

BACKGROUND OF THE INVENTION

A reduction in a heart's cardiac output, i.e., the reduced ability of the heart to output oxygenated blood from the left side of the heart, may result from various abnormalities and diseases of the heart. This reduction in output is typically due to aortic valve disease. There are two major categories of aortic heart valve disease: stenosis and regurgitation. Stenosis involves the narrowing of the aortic outflow tract, causing obstruction to blood flowing from the left ventricle into the ascending aorta. As illustrated in FIG. 1A, the stenosis typically involves the buildup of calcified material 2 on the valve leaflets 4, causing them to thicken and impairing their ability to fully open to permit adequate forward blood flow. Stenotic build up 6 may also occur beneath the valve leaflets 8, i.e., subvalvular stenosis, as illustrated in FIG. 1B. Severe calcification can greatly impair proper functioning of the aortic valve wherein blood outflow is obstructed. Regurgitation, on the other hand, is the retrograde leakage of blood back through the heart valve and into the left ventricle during diastole. Both stenosis and regurgitation of the aortic valve decrease cardiac output which can ultimately lead to hypertrophy of the left ventricle wherein the size of the ventricular chamber becomes enlarged, leading to diastolic dysfunction of the left ventricle, i.e., the impaired ability of the left ventricle to adequately fill with blood. Diastolic dysfunction accounts for about 20% to 40% of heart failures.

Surgical treatments are available to treat diastolic dysfunction of the left ventricle or their precursors (e.g., a defective cardiac valve); however, these treatments have their drawbacks. For example, the most common treatment for stenotic aortic valves is the surgical replacement of the diseased valve, which can be very invasive, requiring dissection of the patient's aorta. A particular drawback of conventional aortic valve replacement procedures is that they require the patient to be placed on the heart-lung machine ("on-pump") wherein the heart is stopped and the surgery is performed through an open chest. Because the success of these procedures can only be determined when the heart is beating, the heart must be closed up and the patient taken off the heart lung machine before verification can be made. If the results are determined to be inadequate, the patient must be put back on cardiopulmonary bypass and the aorta must be reopened. Moreover, the risks and complications associated with open-heart surgery, which involves the use of cardiopulmonary bypass, aortic cross-clamping and cardioplegic arrest, are well known. The most serious risks of cardiopulmonary bypass and aortic cross-clamping are the increase in the likelihood of bleeding and stroke. Also, patients who undergo surgeries using cardiopulmonary bypass often require extended hospital stays and experience lengthy recoveries. Thus, while certain conventional heart surgeries produce beneficial results for many patients, numerous others who might benefit from such surgery are unable or unwilling to undergo the trauma and risks of conventional procedures.

In addition to valve replacement, some patients require reconstruction of the aorta as well due to a variety of factors, e.g., aortic dissection and endocarditis. These valved conduits are integrated and allow the surgeon to fix both the aorta and the valve at the same time. Valved conduits are also used in conjunction with LVAD's (Left Ventricular Assist Devices) to facilitate off loading the heart.

Within recent years, minimally invasive types of procedures for coronary artery bypass surgery have been developed which do not require stopping the patient's heart and the use of cardiopulmonary bypass. While attempts have been made to treat aortic valves off-pump via endovascular procedures, e.g., endovascular balloon valvuloplasty, such procedures may provide only partial and temporary relief for a patient with a stenotic valve. Moreover, the rapid restenosis and high mortality following balloon aortic valvuloplasty have led to virtual abandonment of this procedure.

An endovascular, off-pump approach for treating regurgitant aortic valves has been disclosed (see U.S. Pat. Nos. 3,671,979 and 4,056,854). The procedure involves supplementing the regurgitant valve with a mechanical heart valve placed downstream of the native aortic valve and coronary ostia. The mechanical valve is delivered into the aorta by means of a catheter inserted through the brachial or femoral artery, and is subsequently maintained by a mounting catheter which extends out of the arterial entry site. Due to many complications and drawbacks, this treatment regime is not clinically practiced.

Thus, there is an ongoing need for minimally invasive devices and techniques for treating patients suffering from diastolic dysfunction. As such, it is desirable to provide such a procedure which is relatively simple and is easier to perform than conventional valve replacement procedures and reduces the time and cost of the procedure. Moreover, it is desirable to provide such devices and procedures that obviate the need for cardiopulmonary bypass, can be used on a beating heart, involves endovascular or less invasive surgical techniques, and can be used by surgeons.

SUMMARY OF THE INVENTION

The present invention includes devices, systems, methods and kits for establishing one or more blood flow pathways from the left ventricle of the heart to another native or prosthetic structure. The subject devices include conduits and valves and valved conduits which provide blood flow pathways when placed between the left ventricle to another blood-carrying vessel, such as the aorta or the pulmonary artery, or to a prosthetic or artificial device such as a heart assist device, e.g., an LVAD. The subject systems generally include one or more subject conduits and valves for establishing a blood flow pathway or passage from the left ventricle to another native or prosthetic structure. Also provided are devices and instruments particularly configured for the off-pump surgical implant of such conduit(s) and valve(s), as well as those particularly configured for the off-pump, endovascular delivery and implant of such conduit(s) and valve(s).

The subject methods generally include steps for establishing at least one extra-ventricular blood flow pathway or passage from the left ventricle to another native or prosthetic structure. More particularly, the subject methods include delivering and implanting at least one conduit extending externally from the apex of the heart to the other structure. In one method embodiment, the conduit is established from the left ventricle to the descending aorta. Certain of the subject methods provide for the minimally invasive surgical delivery and implant of such conduit(s), while other subject methods provide for endovascular delivery and implant of such conduit(s).

The present invention further provides kits that include the subject devices and/or systems for carrying out the subject methods. The kits may further include various tools and instrumentation for implanting the subject devices and systems.

A feature of the present invention is the provision of devices and techniques that can be used to facilitate the cardiac output function of the left ventricle. An advantage of the present invention is the elimination of cardiopulmonary bypass for the surgical treatment of left ventricular dysfunction. Another advantage over conventional treatments is the simplicity and ease with which the subject methods are performed. Additionally, the present invention provides substantially reduced procedure times and expenses.

These and other features and advantages of the invention will become apparent to those skilled in the art upon reading the details of the subject systems, devices and methods as more fully described below.

BRIEF DESCRIPTION OF THE DRAWINGS

The following drawings are provided and referred to throughout the following description, wherein like reference numbers refer to like components throughout the drawings:

FIG. 2A illustrates one embodiment of a valved conduit extending from the left ventricle to the descending aorta. FIG. 2B illustrates another embodiment of valved conduit extending from the left ventricle to the descending aorta. FIG. 2C illustrates a system including a conduit extending from the left ventricle to the descending aorta and two valves positioned within the descending aorta.

FIG. 3A illustrates three conduits of FIG. 2C extending in parallel between the left ventricle and the descending aorta and two valves positioned within the descending aorta. FIG. 3B illustrates three valved conduits of FIG. 2A extending in parallel between the left ventricle and the descending aorta.

DETAILED DESCRIPTION OF THE INVENTION

Figure 1A:
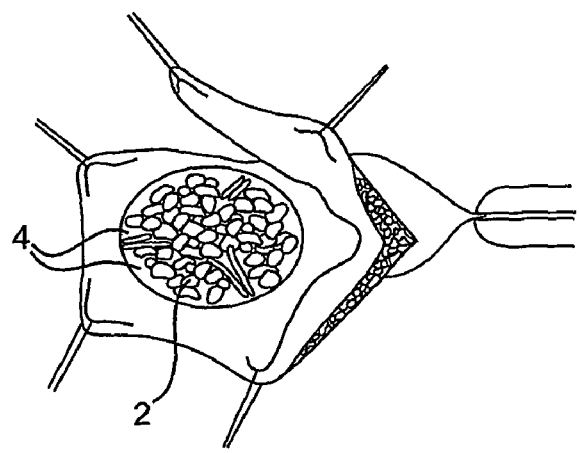
FIGS. 1A and 1B illustrate valvular and subvalvular stenosis, respectively, of the aortic valve.
Figure 1B:
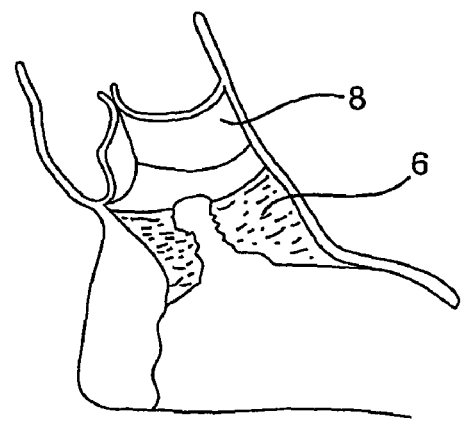

As mentioned above, the present invention includes devices, systems, methods and kits for establishing one or more blood flow conduits from the left ventricle of the heart to the aorta to compensate for a dysfunctional left ventricle.

Before the present invention is described in detail, it is to be understood that this invention is not limited to particular embodiments and applications described, as such may vary within the scope of the scope of the appended claims. For example, the following description of the invention is primarily described in the context of establishing a fluid communication connection between the left ventricle of the heart and the descending aorta; however, such description, with certain obvious modifications to the invention, is also intended to apply to such connections between the left ventricle and another natural or native structure, e.g., the ascending aorta; between another chamber of the heart to another native blood conduit, e.g., from the right ventricle to the pulmonary arteries; or from another organ or fluid carrying vessel to another organ or fluid-carrying vessel. It is also contemplated that present invention be applicable for establishing fluid communication between a natural or native structure to an artificial or prosthetic device, e.g., LVAD. It is also to be understood that the terminology used herein is for the purpose of describing particular embodiments only, and is not intended to be limiting, since the scope of the present invention will be limited only by the appended claims. Furthermore, the methods recited herein may be carried out in any order of the recited events which is logically possible, as well as in the recited order of events.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

DEFINITIONS

The terms "downstream" and "upstream," when used herein in relation to the patient's cardiovascular system, refer to the direction of blood flow and the direction opposite that of blood flow, respectively. In the arterial system, downstream refers to the direction further from the heart, while upstream refers to the direction closer to the heart. When these terms are used herein in relation to a conduit, valve or other implant or the placement thereof, downstream refers to the portion of such conduit, valve or other structure which is furthest from the heart, and upstream refers to the portion of such conduit, valve or other structure which is closest to the heart.

The terms "proximal" and "distal," when used herein in relation to instruments used in the procedure of the present invention, respectively refer to directions closer to and farther away from the operator performing the procedure.

Devices and Systems

Referring now to FIGS. 2A-C and 3A-C, various exemplary systems of conduit and valve arrangements of the present invention are illustrated in operative use, i.e., in fluid communication between the left ventricle 12 of the heart 10 and the descending aorta 18 to bypass aortic valve 16. As indicated by directional arrows 30a, in a normal functioning heart, the left ventricle 12 pumps blood through the aortic valve 16 into the ascending aorta 14 which flows in an antegrade direction into the bracheocephalic trunk 34 to the brain and through the descending aorta 18 to the remainder of the body.

Figure 2A:
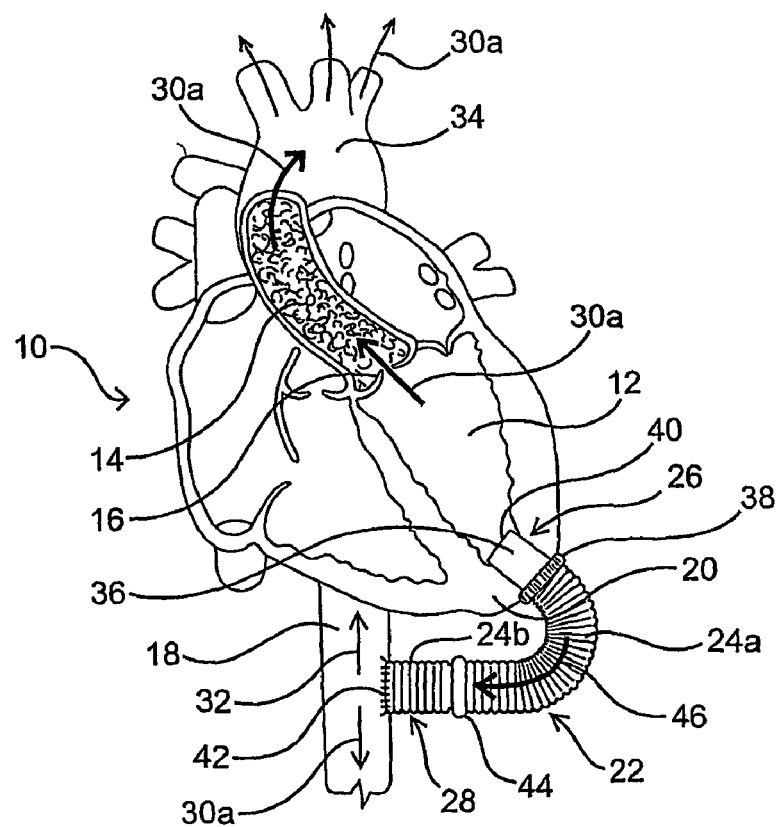
FIGS. 2A-C illustrate exemplary embodiments of systems of the present invention which establish a flow path from the left ventricle of a heart to the descending aorta.

FIG. 2A illustrates an apparatus 22 of the present invention including a two piece conduit 24 having portions 24a and 24b, collectively referred to as conduit 24. The conduit 24 having a first or upstream end 26 and a second or downstream end 28. Upstream end 26 includes an extension portion 36 which, here, extends through the myocardial wall of the heart at apex 20 and terminates at an opening 40. Upstream end 26 further includes a retention or fixation means 38 which may take a variety of forms such as an external retaining ring or radial flange which may be sutured, glued, clipped or stapled or the like to the epicardial surface of the heart. The retention or fixation means 38 may alternatively be placed internally within the left ventricle. Such internal fixation or retention means may take the form of an internal retaining ring or flange which may be affixed to the endocardial surface of the left ventricle in a manner similar to that described above with respect to an external retaining ring or may be held in place by the pressure within the left ventricle and the by constriction of the myocardium.

All configurations of downstream end 28 have an opening therein, however, the exact construct of downstream end 28 of conduit 24 is dependent upon the structure to which it is to be connected. For example, when the structure is the descending aorta, as in FIG. 2A, downstream end 28 may be configured to have a free end which is attachable by means of an anastomosis procedure, i.e., by using sutures 42, magnets or other anastomotic connectors known in the art. Where downstream end 28 is to be affixed to an LVAD or other device, certain obvious, alternative configurations of end 28 are required. Apparatus 22 further includes a valve 44 which is positioned along the length of conduit 24 between ends 26 and 28. Valve 44 serves to provide one-way flow of fluid or blood in the direction of arrow 46 during systolic function of the heart, thereby providing retrograde flow within the descending aorta 18 to the brain, as indicated by arrow 32, as well as antegrade flow to the body, as indicated by arrow 30a. During diastolic phase of the heart, valve 44 is closed. Here, valve 44 serves as a junction for the interconnection of separate conduit portions 24a and 24b, however, such a juncture may be provided at other locations along the length of conduit 24. While a portion of valve 44 is shown outside conduit 44, valve 44 may be configured to be completely within conduit 24 such that conduit 24 is a seamless unitary piece.

Figure 2B:
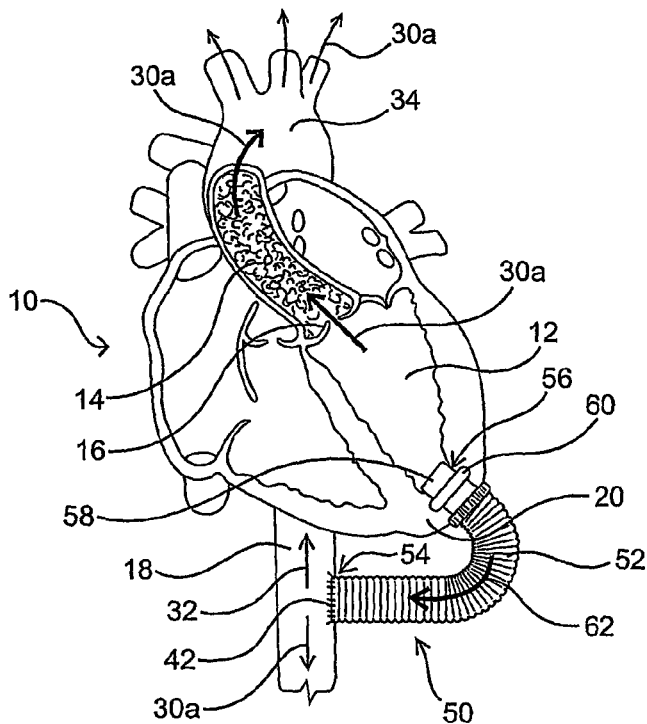

FIG. 2B shows an alternative configuration of an apparatus of the present invention. Apparatus 50 includes single-piece conduit 52 having a first or downstream end 54 and a second or upstream end 56. Downstream end 54 is configured similarly to downstream end 28 of FIG. 2A. Upstream end 56 has an extension portion 58 extending through the heart wall and in fluid communication the left ventricle chamber 12. Here, a valve 60 is located within extension portion 58 rather than in conduit 52 so as to be substantially adjacent the apical opening. During systolic function of the heart, valve 60 directs blood flow into conduit 52 in the direction of arrow 62 and into the descending aorta 18 in both antegrade (arrow 30a) and retrograde (arrow 32) directions. During diastolic function, valve 60 remains closed.

Figure 2C:
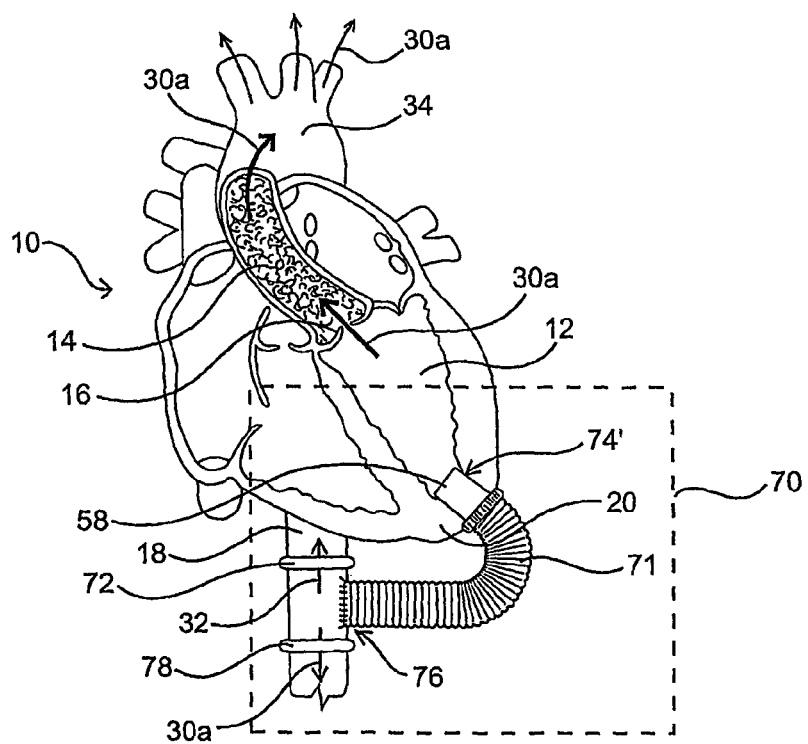

FIG. 2C illustrates yet another configuration of an apparatus or system of the present invention. Here, the system includes a single-piece conduit 70 having upstream and downstream ends 74 and 76, respectively, which are similar to their corresponding components in FIG. 2A. In this embodiment, the conduit is not valved, but instead, two one-way valves 72 and 78 have been operatively implanted within descending aorta 18 on opposing sides of the downstream end 76 of conduit 71. During systolic function of the heart, valve 72 provides blood flow from conduit 70 in a retrograde direction (arrow 32) while valve 78 provides blood flow from conduit 70 in an antegrade direction (arrow 30a). During diastolic function, both valves are closed.

Figure 3A:
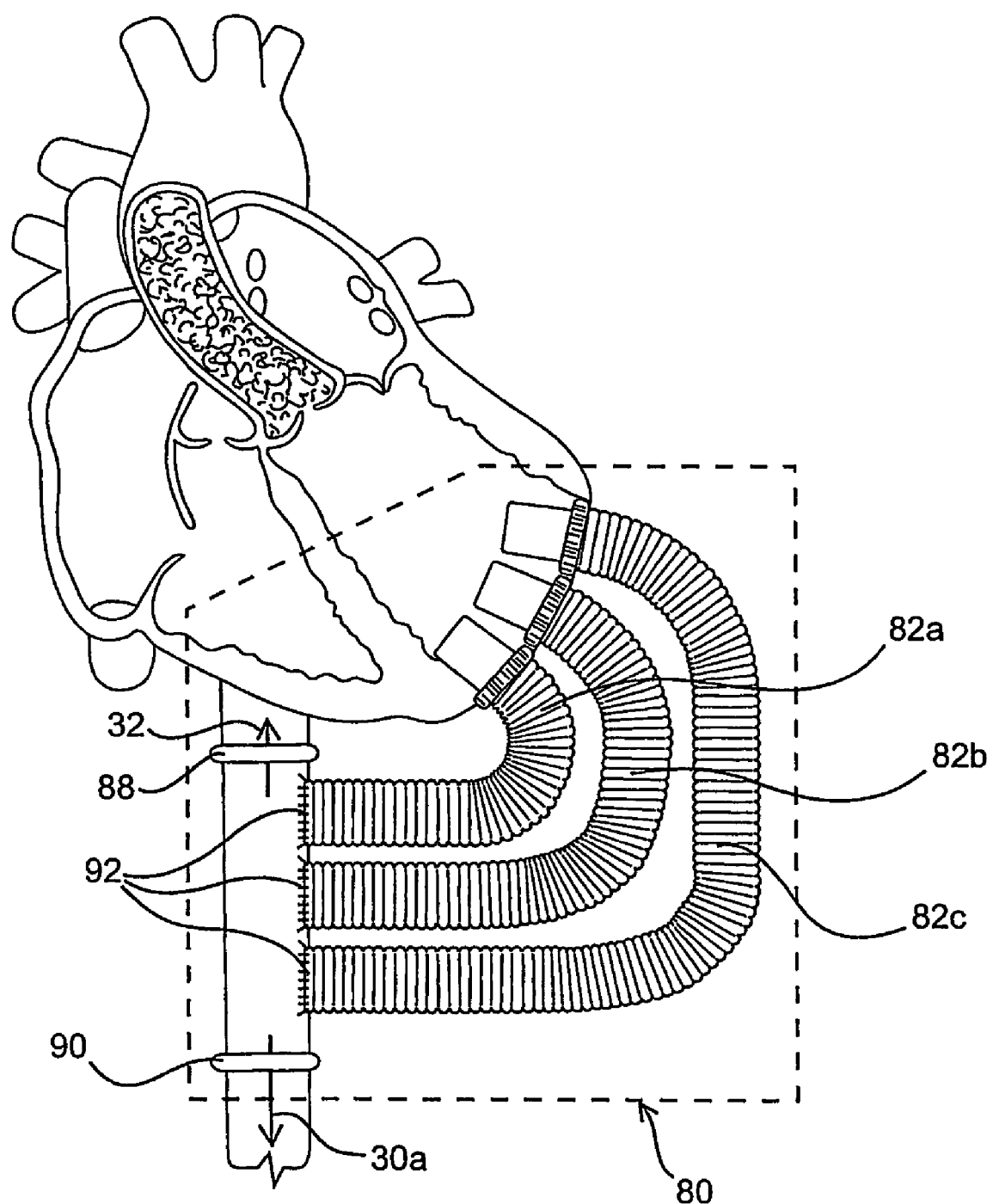
FIGS. 3A and 3B illustrates exemplary embodiments of systems of the present invention which establish more than one flow path from the left ventricle of a heart to the descending aorta.
Figure 3B:
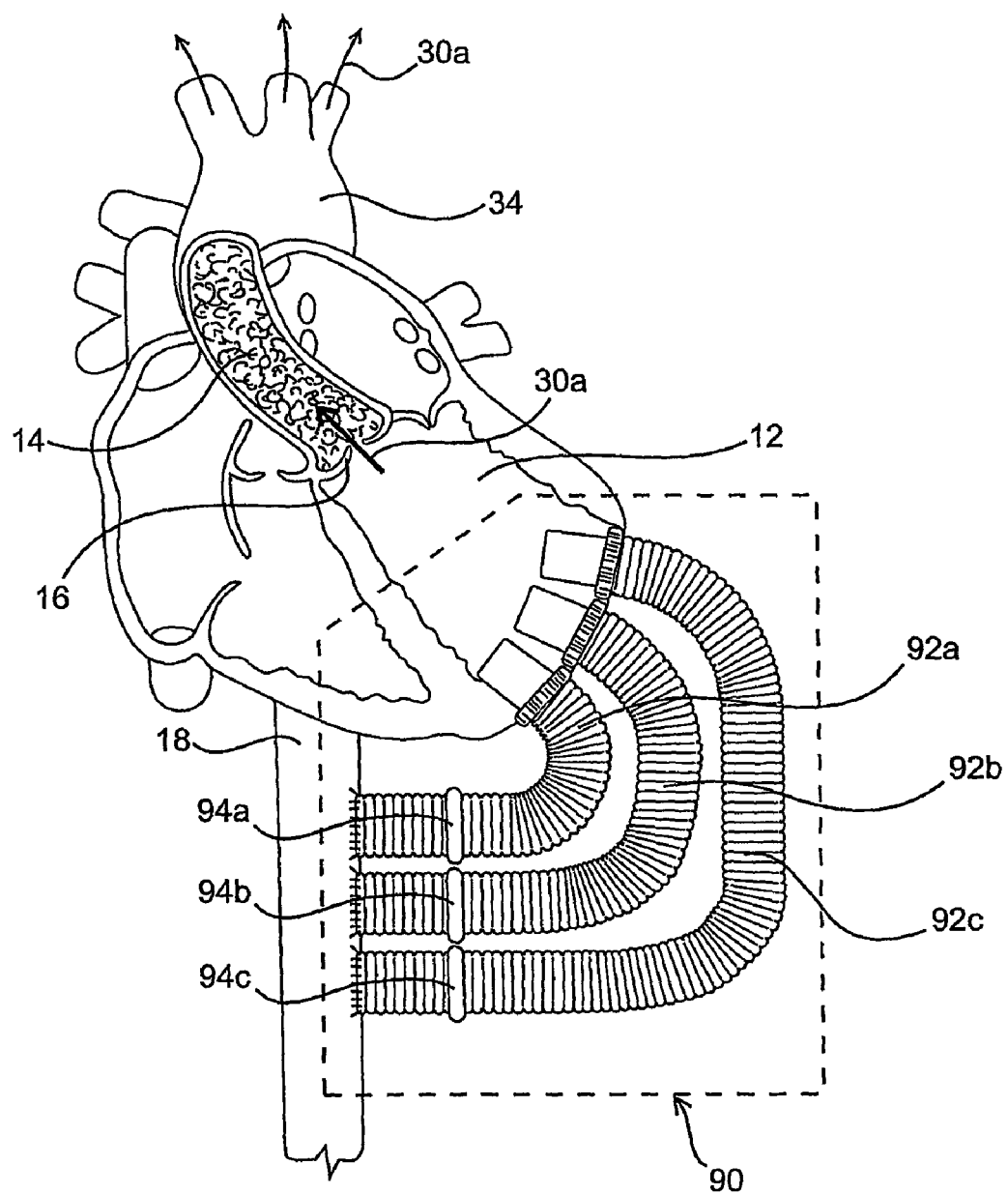

Referring now to FIGS. 3A and 3B, other systems of the present invention are illustrated, each having a plurality of conduits extending from the left ventricle to the descending aorta. While each of these systems is illustrated with three conduits, any necessary or appropriate number of conduits may be used. Additionally, while the conduits are illustrated to be parallel with respect to each other, other arrangements are possible, e.g., each conduit may be tangential with each of the other two conduits, and may be placed radially around the descending aorta.

In FIG. 3A, a system 80 is provided wherein each of its three conduits 82a, 82b, and 82c has a configuration similar to conduit 71 of FIG. 2C. System 80 further includes two valves 88 and 90 positioned within the descending aorta where valve 88 is positioned upstream of the downstream end openings 92 and valve 90 is positioned downstream of the downstream end openings 92. In FIG. 3B, a system 90 is provided wherein each of its three conduits 92a, 92b, and 92c has a configuration similar to that of conduit 24 of FIG. 2A in which each has a valve 94a, 94b and 95c, respectively, within its lumen.

The number of conduits and the size of the conduit(s) may be preferentially determined based on the degree of stenosis, the ideal area of access/fixation and other various factors.

Conduits

The conduits of the present invention may be as rigid or flexible as desired by the surgeon or as necessary for the application at hand. Certain embodiments of conduits are substantially flexible along the majority of their lengths so as to accommodate the heart's beating motion and the adjacent anatomy but are rigid enough to withstand deformation from forces caused by the contraction of the myocardium. Such embodiments may provide some rigidity at their ends for establishing a more fixed connection between structures. Certain other embodiments may be substantially rigid along their lengths. The flexibility/rigidity of a particular conduit will depend in part on the application at hand and the type and location of the structure to which the downstream end of the conduit is connected. In other embodiments, the conduits may be composed of biologic tissue and will take on the characteristics of the base tissue unless otherwise treated or reinforced.

The type of material used for the conduits will also depend on the desired flexibility/rigidity of the conduits. Conventional artificial conduits used with LVADs, such as those disclosed in U.S. Pat. No. 6,001,056, may be used. These conduits are fabricated of a flexible, knitted or woven polyethylene terephthalate fabric, polypropylene or PTFE. The flexible material may be formed over a coiled structure. In certain embodiments, the conduits are sealed with or impregnated with a biocompatible sealing material. For example, the sealant may comprise a thin biocompatible collagen coating on the inner lumen wall to render the fabric more leak resistant. The collagen coating is eventually absorbed into the patient's blood stream and is replaced with a natural coating of blood cells, serum protein and other elements of the blood which mimic the endothelium. For more rigid conduits, the conduit is preferably formed of titanium or another smooth, biocompatible material in order to resist thrombus formation. The external surface of the conduit may be coated or wrapped with a tissue growth-inducing material to facilitate adhesion to the conduit by adjacent tissues. An example of such a conduit is disclosed in U.S. Pat. No. 5,984,956. For tissue-based conduits, a variety of autografts, homografts, xenografts may be used for the conduit.

The conduits may also have the ability to diffuse drugs or other agents at a controllable rate to within the lumen of the conduit, particularly at the site of the valve. One or more therapeutic agents may be added to the conduit's fabric during the manufacturing process fabrication or a coating containing such therapeutic agents may be applied to the conduit after it has been fabricated by means of spraying, dipping or other suitable means. Suitable therapeutic agents for use with the subject fasteners include, but are not limited to, dexamethasone, tocopherol, dexamethasone phosphate, aspirin, heparin, coumadin, urokinase, streptokinase and TPA, or any other suitable thrombolytic substance to prevent thrombosis at or around the points of attachment to tissue and the valve. The subject conduits may also include materials such as paralyne or other hydrophilic substrates that are biologically inert and reduce surface friction.

Furthermore, the conduits may be configured to enable fluoroscopic visualization while delivering and operatively placing the conduits. The conduits may comprise one or more radio-opaque materials added to the conduit fabric during the fabrication process or a coating containing radio-opaque material may be applied to the conduit after it has been fabricated. Alternatively, the conduit may be provided with one or more radiopaque markers. Any suitable material capable of imparting radiopacity may be used, including, but not limited to, barium sulfate, bismuth trioxide, iodine, iodide, titanium oxide, zirconium oxide, metals such as gold, platinum, silver, tantalum, niobium, stainless steel, and combinations thereof.

The conduits of the present invention may have any suitable shape such as an elbow or L-shape, an S-shape or, where substantially flexible, may take on any desirable shape upon implantation within a patient. The diameter and overall length dimensions of a particular conduit will depend on the application at hand, the location and size of the structure to which the downstream end of the conduit is to be attached, and the number of conduits to be employed. For example, if using a single conduit, such as those illustrated in FIGS. 2A, 2B and 2C, for interconnecting the left ventricle to the descending aorta, the diameter of the conduit is typically in the range from about 17 mm to about 33 mm, and more typically in the range from about 19 mm to about 31 mm. The overall length of such a conduit is typically in the range from about 5 cm to about 15 cm, and more typically in the range from about 7 cm to about 12 cm. If, however, the system embodiments of FIGS. 3A and 3B are employed, the diameter of such conduits are typically in the range from about 4 cm to about 10 cm, and more typically in the range from about 5 mm to about 10 mm. While the lengths of the several conduits may vary from each other, they will typically be within the ranges recited for single-conduit systems.

Figure 4:
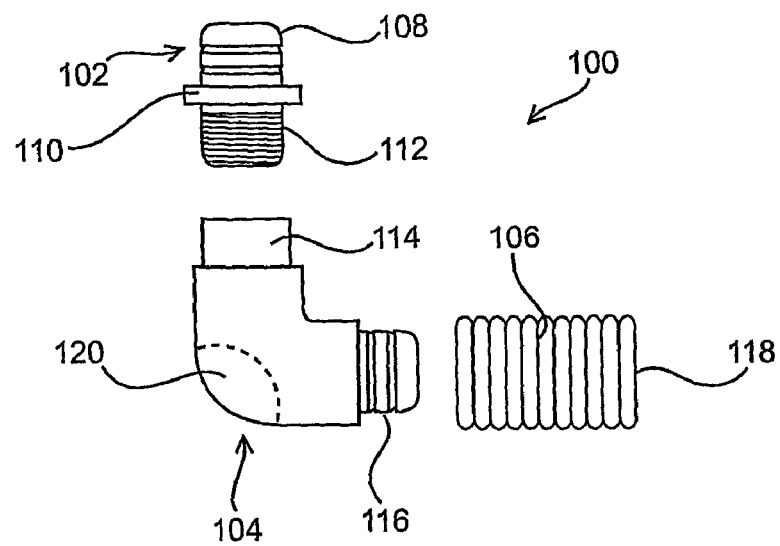
FIG. 4 is an exemplary embodiment of an angled conduit of the present invention.

An example of a conduit for use according to the principles of the present invention is illustrated in FIG. 4. Conduit 100 is shown having three separate but connectable components, an apical fixation portion 102, a transition or angled portion 104 and an extension or graft portion 106. Apical fixation portion 102 comprises the upstream end of conduit 100. Portion 102 includes an internal extension 108 which is retained within the myocardial wall, an external retention ring 110, as described above, and a threaded end 112 for threaded engagement with upstream end 114 of angled portion 104. The elbow configuration of angled portion 104 can be selectively directed relative to the longitudinal axis defined by portion 102 and, thus, is selectively directable relative to the left ventricle to facilitate attachment of graft portion 106 to a structure at a downstream location. The angle defined by angled portion 104 may be any angle suitable for the application at hand, but typically ranges from about 45° to about 135°. Optionally, angled portion 104 may have a sealable port or valved opening 120 which provides access to within conduit 100 along the longitudinal axis defined by portion 102 as well as along the longitudinal axis defined by portion 106. The valved or sealable access allows for the insertion of tools for use during the implantation process to be delivered upstream to the left ventricle and/or downstream to the descending aorta while preventing the leakage of blood. Angled portion 104 has second or downstream end 116 configured for engagement with graft portion 106. Here, graft portion 106 is provided as a flexible tubular structure. The open downstream end 118 of graft portion 106 may be anastomosed or otherwise connected to the lumen of a vessel or the chamber of an organ or device. A valve (not shown) may be positioned at any suitable location as described above, e.g., between angled portion 104 and graft portion 106 or at the downstream end 118 of graft portion 106.

Valves

Any suitable valve, preferably a mechanical valve, may be used with the systems of the present invention. Mechanical heart valves include caged-ball valves such as the Starr-Edwards valves, bi-leaflet valves such as those manufactured by St. Jude, and tilting disk valves such as the Bjork-Shiley, Medtronic-Hall and Onmiscience valves. Each of these valves is attached to a sewing ring, usually made of Dacron.

In use with the present invention, the sewing ring may be used to attach the valve, alone or with an attached conduit, to the desired location, or may otherwise be modified to be affixed within a lumen of a conduit. Alternatively, a valve may be integrally fabricated within a conduit. The exact number and placement of the valves relative to the conduit will be dependent upon the specific application and structures being interconnected. For example, a valve may be placed in the apical portion (i.e., the upstream end) of a conduit, such that, upon implantation, it is located either on the surface of the epicardium, within the myocardium or is adjacent with the inside wall of the ventricle (see FIG. 2B). Alternatively, the valve may be placed at the downstream end of a conduit such that, upon implantation, it is located either within the descending aorta or external but adjacent to the conduit attachment site in the descending aorta (see FIGS. 2A and 3B). Also, as discussed with respect to FIGS. 2C and 3A, the valves may be implanted with the descending aorta independently from the conduit. Finally, in certain embodiments of the present invention, the valve may be insertable into and selectively positionable within the conduit's lumen. This embodiment, as discussed below, facilitates the attachment of the conduit to the interconnected structures or organs prior to insertion and permanent placement of the valve.

Methods and Devices for Improving Cardiac Output

The methods of the present invention are directed to improving cardiac output, and involve the implantation of the systems and devices described above. The implantation methods are performed with the use of various devices and tools for the delivery and fixation of the subject system and devices, e.g., conduits, valves, valved conduits, etc., which allow the implantation to be done without cardiopulmonary bypass and while the patient's heart is beating. Certain of the methods employ a direct vision, i.e., surgical, or endoscopically-assisted, approach while others are performed endovascularly under fluoroscopy. Still others involve a combination of both approaches.

The various methods will now be discussed in detail with illustrations and descriptions of various exemplary implantation tools of the present invention which may be optionally used to carry out the steps of the implantation methods. It should be noted that while an attempt has been made to describe methods of the invention as broadly as possible, certain acts and steps may vary from the description depending on whether on certain factors including but not limited to the application at hand, whether a one-piece or multiple-piece conduit is employed, whether the valve is integral with the conduit, if not integral, the number and location of valves to be placed, surgeon preference, etc.

Direct/Endoscopic Approaches

A direct surgical and/or endoscopic approach will be generically described, except where indicated, in the context of using any conduit embodiment of the present invention. Additionally, in the following description, the upstream or ventricular connection of the conduit is described first and the downstream or aortic connection is described second, however, such order is not required and the steps may be performed in reverse order.

Initially, access is made through the chest cavity to expose the left ventricle including the apex of the heart and the descending aorta. Direct access may be made by any appropriate incision including a sternotomy, thoracotomy or mini-thoracotomy or the like. One approach is to place the patient in the right lateral decubitus position and enter the thorax through the fifth intercostal space. Alternatively or in addition to the direct access site, one or ports may be positioned in the chest cavity, such as between adjacent ribs, for the delivery of an endoscope and other instrumentation.

Next, an appropriate location on or substantially adjacent the apex is selected for attachment of the conduit. This may be accomplished by an external evaluation of the apical region involving visual and/or tactile assessment of the heart. This step may also be determined by endovascular means such as by the use of catheter-based guidance/imaging systems, e.g., fluoroscopic imaging, which are well known in the art. Such endovascular means of assessing and selecting an upstream conduit attachment site is discussed in greater detail below with respect to the endovascular methods of the present invention.

Next, an opening is made within the myocardium at the selected upstream attachment on the left ventricle. The Seldinger technique provides a convenient way of establishing initial access to within the left ventricle while minimizing blood loss through the entry site. With the Seldinger technique, a small gauge needle is introduced through the wall of the myocardium and a guide wire is introduced through the needle and delivered to within the left ventricular chamber. After proper placement of the guide wire, the needle is withdrawn and the distal end of the guide wire is left in place within the heart wall to provide a tether or "rail" over which other tools or devices may be delivered.

At this point in the method, the order of the subsequent steps generally depends on the type of conduit being used. For certain conduit embodiments, it is preferable to expand or dilate the opening defined by the placed guidewire prior to affixing the conduit to the left ventricle. To do so, however, it is necessary to ensure that minimal blood escapes from the left ventricle which is actively pumping. Accordingly, a sealing means is first delivered over the guidewire to within the left ventricular chamber.

Figure 5A:
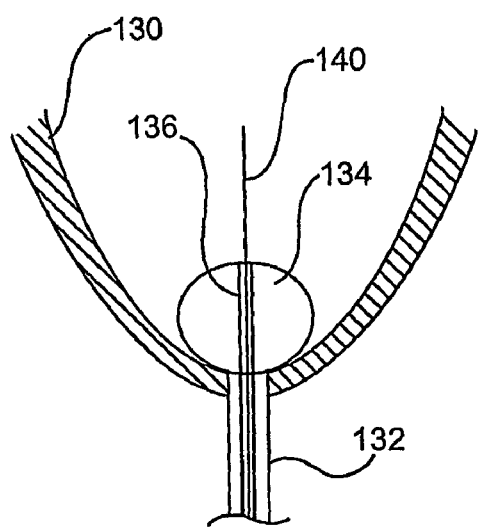
FIG. 5A illustrates an embodiment of an access and sealing device of the present invention which employs a balloon sealing member.
Figure 5B:
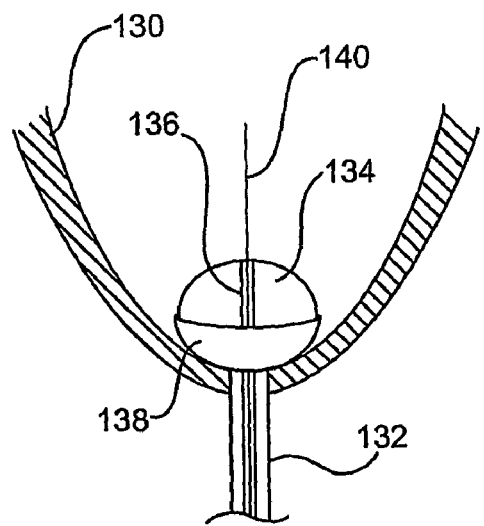
FIG. 5B illustrates another embodiment of an access/sealing device of the present invention similar that of FIG. 5A but which further includes a backstop mechanism.

FIGS. 5A and 5B illustrate balloon sealing mechanisms operatively positioned within the left ventricle 130 of a heart and which are suitable for use with the subject methods. The sealing mechanism includes a catheter 132 and an inflatable balloon 134 at the distal end of catheter 132. Extending within the length of catheter 132 and balloon 134 is a guide wire lumen 136 for accommodating guide wire 140 over which catheter 132 and balloon 134, in an uninflated state, are translated until balloon 134 is operatively positioned inside the left ventricular wall. Once within the left ventricle chamber, balloon 134 is inflated via an inflation lumen (not shown) extending along the length of catheter 132. When inflated, balloon 134 substantially seals the opening within the left ventricle 130. The sealing mechanism of FIG. 5B is similar to that of FIG. 5A but further includes an expandable cup, shield or plate 138 about the proximal side of balloon 134 which expands upon inflation of balloon 134 to provide a substantially stiff back stop which acts to shield the balloon and to prevent over penetration (and minimize the risk of puncture) by other tools used for the implantation procedure.

Figure 6A:
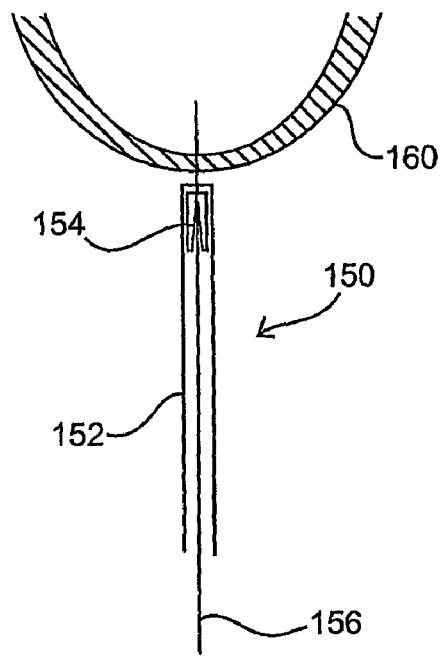
FIGS. 6A and 6B illustrate use of another embodiment of an access/sealing device of the present invention. This embodiment employs a wire mesh sealing member.
Figure 6B:
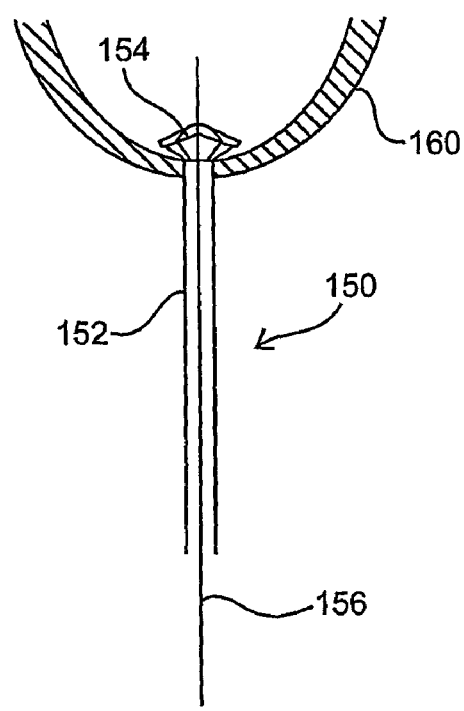

FIGS. 6A and 6B illustrate another sealing means 150 suitable for use with the present invention. Sealing means 150 includes a catheter 152 having an expandable wire mesh or nitinol basket 154 preferably coated with a flexible, fluid impermeable material. In an unexpanded or undeployed state, basket 154 has a low profile, as shown in FIG. 6A, which is positionable within catheter 152 and deliverable over guidewire 156 through the opening within the ventricular wall 160 defined by guide wire 156. Once inside the left ventricular chamber, as shown in FIG. 6B, wire mesh 154 can be expanded to form a seal over or flush against the inside wall as well as to provide a backstop.

While the sealing steps may be performed under fluoroscopic visualization to properly guide the sealing mechanism into the left ventricle, other means may be used to determine when sealing means has completely entered into the left ventricle. For example, a feedback lumen may be provided in the catheters of the just described sealing devices which allows for a very slight volume of blood to drip out of the left ventricle thereby indicating that the left ventricle chamber has been reached.

Once access is established and a sealing member is in place, a conduit may be affixed to or implanted within the myocardium wherein a target attachment section of the myocardium is opened, removed or cored to accommodate the upstream end of a conduit. Although not required, a temporary fixation device may be employed as a preliminary step to permanently fixing the conduit to the heart. For example, the conduit can be provided with an upstream end having a permanent or removable magnet which can be positioned, as described above, in lieu of a separate second magnet. The conduit will then be properly aligned while the myocardial opening is enlarged and/or the conduit is permanently affixed to the myocardium by means and methods as described below.

Figure 7:
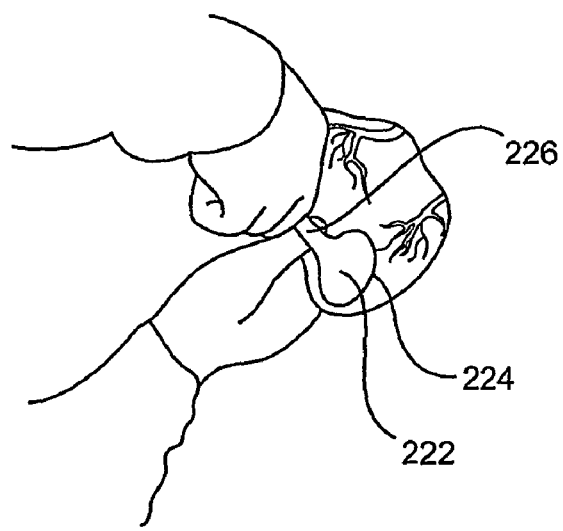
FIG. 7 illustrates an embodiment of a temporary conduit fixation device of the present invention.

FIG. 7 illustrates a temporary conduit fixation or alignment device in the form of suction device 222 having an annular distal end 224 and a proximally extending hollow shaft 226. Suction device is operatively connected to a source of negative pressure so that distal end 224 adheres to the surface of the heart. Hollow shaft 226 provides a delivery and working channel through which a conduit may be inserted, delivered and properly aligned with a selected entry site within the myocardium. Additionally, instruments may also be delivered through the working channel for coring the myocardium and for permanently affixing the conduit.

Figure 8A:
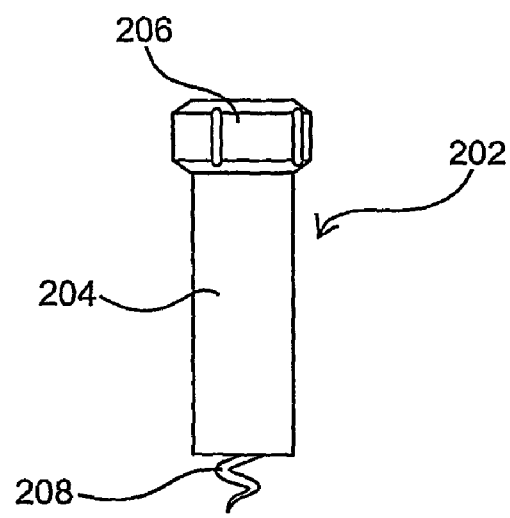
FIG. 8A illustrates another embodiment of a temporary fixation device of the present invention.

Another temporary fixation device for use with the present invention is illustrated in FIG. 8A. A "corkscrew driver" temporary fixation device 202 is provided which includes a cylindrical sheath or tube 204, a knob, handle or cap 206 at a proximal end of tube 204 and a rigid, helically wound coil 208 affixed to the underside of cap 206 and extending coaxially through tube 204. When cap 206 is turned or rotated, coil 208 is caused to penetrate through the myocardium. Tube 204 may have a sharpened distal edge 215 which can penetrate and core the myocardium.

Figure 8B:
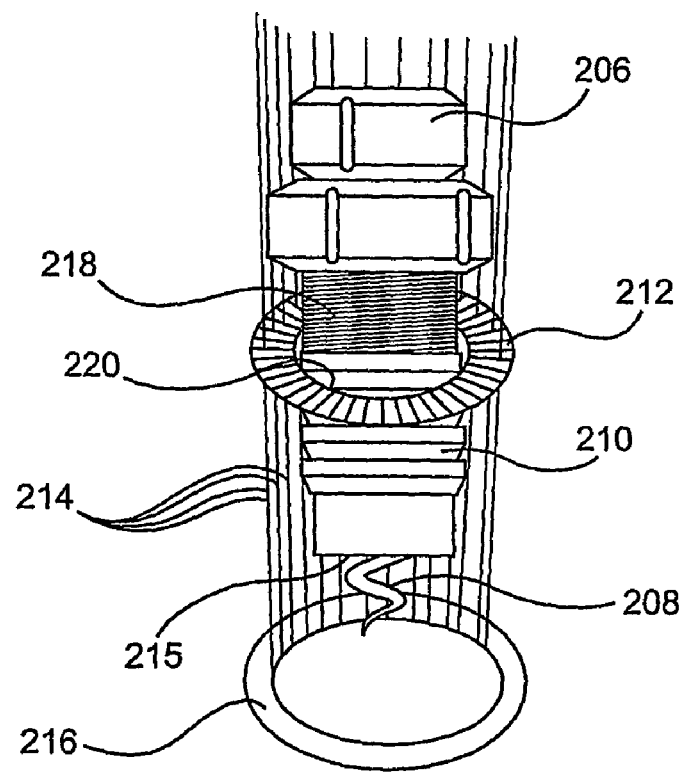
FIG. 8B illustrates operative engagement of the fixation device of FIG. 8A with a conduit of the present invention.

As illustrated in FIG. 8B, fixation device 202 is configured to coaxially engage within the lumen of a conduit 210 so as to temporarily fix the position of conduit 210 against the myocardial wall while permanent fixation can be established. Here, a permanent fixation means, such as sewing ring 212, may be carried about conduit 210 and placed about the cored section of myocardium 216 on the exterior surface of the heart. Once properly placed, the ring may be sutured in place by sutures 214. Sewing ring 212 has a threaded interior surface 220 which may be threadably engaged with external threads 218 of conduit 210 to properly and securely seat cannula 210 within the cored myocardium 216.

Figure 9:
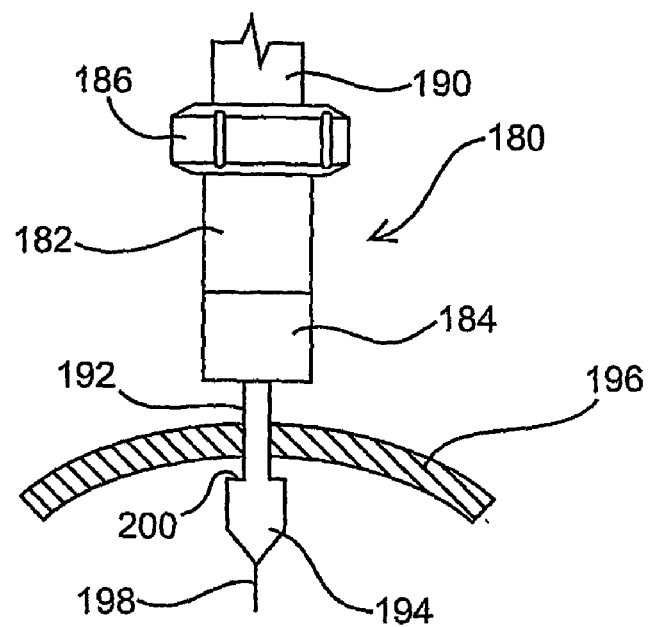
FIG. 9 illustrates an embodiment of a tissue coring device of the present invention.

A separate puncturing, incising or coring mechanism may also be used to remove a piece of the myocardial wall. FIG. 9 illustrates such a coring device 180 which includes cylindrical shaft or cannula 182 having a rotatable knob or handle 186 at a proximal end and a sharpened edge about a distal end 184. Coaxially engaged within cannula 182 is dilator mechanism 190 having a shaft 192 terminating distally in a dilator tip 194 having a pointed tip and proximal shoulder 200. Shaft 192 has a guidewire lumen (not shown) extending through its entire length. In use, dilator mechanism 190 is tracked over a guidewire 198 until dilator tip 194 is caused to penetrate the myocardial wall 196. While pulling back on dilator 190, so that proximal shoulder engages the interior wall 196 of the left ventricle, coring device 180 is translated distally over dilator mechanism 190 and either pushed forward or rotated so as to core out a target section of the myocardial wall. Dilator mechanism 190 may then be pulled proximally to withdraw the cored piece of tissue from cannula 182.

Figure 10A:
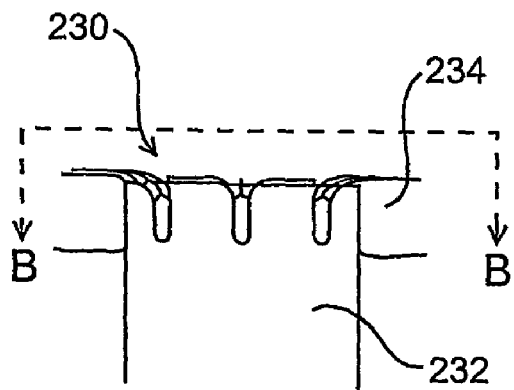
FIG. 10A is a cross-sectional view of an embodiment of a permanent conduit fixation device of the present invention showing fixation of a conduit within the myocardium.
Figure 10B:
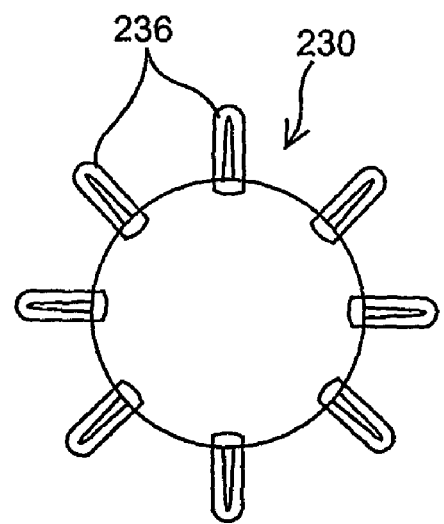
FIG. 10B illustrates a view of the device of 10A along the lines B-B of FIG. 10A.

In addition to the external fixation ring 212 discussed above with respect to FIG. 8B, other permanent fixation means may be used to affix a conduit to the heart. For example, a bio-adhesive may be used to secure ring 212 to the surface of the myocardium or to directly adhere conduit 210 within the cored site. Alternatively, art anastomotic-like connector such as connector 230 of FIGS. 10A and 10B may be employed to affix the conduit 232 to within the myocardium wall 234. Connector 230 has an annular body having radially extending clips or fingers 236 which, by penetration or compressive force, are affixed to the surrounding tissue. Other connectors, such as those disclosed in U.S. Pat. No. 5,676,670 and PCT International Publication No. WO 97/27898, may be used to carry out the methods of the present invention.

At this point in the implant procedure, the sealing mechanism, if one has been used, may remain in place on the inside of the left ventricle or may otherwise be removed and the upstream portion of the conduit may be externally clamped (if flexible enough) or internally plugged (if not flexible enough) to prevent leakage of ventricular blood.

In certain methods of the present invention, the act of establishing an opening in the myocardium, as well as an opening in the descending aorta (discussed below), may be performed after the conduit has been securely fixed in place at both the upstream and downstream ends. Such may be accomplished with the angled conduit embodiment of FIG. 4. After the ends are permanently affixed, the coring or incising of the left ventricle and descending aorta may be accomplished with tools which are inserted into sealed port 120. While the method embodiment described thus far involves the discrete steps of affixing the upstream end of the conduit the left ventricle wall and of forming the opening at the connection site, the acts of affixing and forming the opening may be performed integrally or simultaneously with each other.

After establishing a connection between the conduit and the myocardium, a connection may be established between the downstream end or piece of the conduit and the descending aorta. First, the target downstream attachment or connection site on the descending aorta is selected. As discussed above with respect to establishing an upstream connection between the left ventricle and the conduit and creating an opening in the myocardium, the order in which a downstream connection and an opening in the descending aorta are made may vary. For example, the downstream end of the conduit may be attached to the descending aorta prior to creating an opening in the descending aorta, or visa-versa. With either approach, when creating the connection opening within the aorta, a substantially bloodless space must be defined within the descending aorta at the selected conduit connection site. This may be accomplished by externally clamping the descending aorta at a location upstream of the connection site as well as at a location downstream of the connection site.

For system embodiments having one or more valves which are independent of the conduit, such as those of FIGS. 2C and 3A, the one or more valves can be implanted in the descending aorta in a conventional manner, i.e., the valves are inserted into the incised or cored opening, selectively positioned within and along the length of the descending aorta and then sutured in place by means of a sewing ring, or through a percutaneous/catheter based approach whereby the valve is threaded through a vessel into proper position and then expanded into place.

The downstream end of the conduit may now be affixed to the opening within the descending aorta. The means discussed above for temporarily/permanently affixing the conduit to the left ventricle may be employed for affixing the conduit to the descending aorta. These include suturing, bio-adhesives, magnets, anastomotic-type connectors, stapling, etc. After permanent fixation of the conduit to the descending aorta has been completed, the conduit and/or the left ventricle and/or the descending aorta may be unclamped, unplugged and/or unsealed, as the case may be, thereby allowing blood to flow from the left ventricle through the conduit and into the descending aorta.

For embodiments of the implants of the present invention which provide for valves which may be inserted into a conduit subsequent to fixation of the conduit, the valve may now be inserted into the conduit and positioned at a selected location within the conduit. The external clamps or internal occluders may at this point remain in place or be removed from the left ventricle and descending aorta, respectively, and the conduit clamped or plugged at the upstream and/or downstream ends to prevent the escape of blood. Once both tissue openings are created, sealed port 120 may be permanently sealed by an adhesive patch, a snap fit cap or other like means.

Endovascular Approaches

An endovascular or catheter-based approach to establishing blood flow from the left ventricle to the descending aorta is primarily described in the context of a single-piece conduit having an annular magnet at each of its ends. The implanted system further includes at least one valve which may be integral with the conduit, separate from but positionable within the conduit, or separate from the conduit and positionable within the descending aorta. Unless otherwise indicated each of the acts described below is catheter-based, meaning that the instrument or device being used is delivered via catheter to the operative or target site, with the use of guidewires, guiding catheter or both and a guidance/imaging system.

Two approaches are available to obtain access to the left ventricle. One approach involves forming the opening in the wall of the left ventricle from the outside of the heart (the "outside-to-inside" approach). The other approach involves forming the left ventricular opening from the inside of the chamber of the left ventricle (the "inside-to-outside" approach). While the inside-to-outside approach requires endovascular entry into the chamber of the left ventricle, the outside-to-inside approach does not; however, the outside-to-inside approach may nonetheless involve access to within the left ventricle for the purpose of properly aligning the conduit at a selected upstream connection site on the left ventricular wall. For example, a guiding catheter or the like having radiopaque markers may be delivered under fluoroscopy to within the left ventricle and engaged or anchored at a target site selected by the physician. The physician can then use the radiopaque marker as a beacon when delivering other instrumentation to that site, either at the inside or outside surfaces of the left ventricle. Because the area within the chest cavity outside the heart and the vascular system, e.g., the space between the external surface of the left ventricle and the outside surface of the descending aorta, cannot be visualized by fluoroscopy, it may be desirous to use an endoscope, via a port within the chest cavity. The outside-to-inside approach may, however, not involve any endovascular access to the left ventricle, relying solely on endoscopic visualization with respect to maneuvers or steps involving contact with the left ventricle (maneuvers within the descending aorta may still be done under fluoroscopy).

Whether using an inside-to-outside or an outside-to-inside approach to form the opening for the upstream connection site in the left ventricular wall, i.e., the upstream connection site, the various remaining steps of the subject methods are the same or similar except where indicated. In either approach, access to the arterial vascular system is first established by percutaneously accessing a peripheral artery, such as the femoral artery. Whether for guidance purposes or for creating an opening in the left ventricle, one of two endovascular routes may be taken from the femoral entry site to arrive in the left ventricular chamber. In one route, the guidewire or catheter is translated in an antegrade direction through the vena cava and into the right atrium, across the atrial septal wall into the left atrium, and across the mitral valve into the left ventricle. In an alternative route, the guidewire or catheter is delivered in a retrograde direction through the descending aorta, over the aortic arch and is made to cross the aortic valve into the left ventricle.

The conduit may be affixed or attached to the left ventricle prior to forming the opening in the ventricular wall. Prior to fixation, however, the conduit is preferably properly aligned at the selected connection site. To this end, alignment tools, e.g., magnets, may be employed to identify the selected conduit attachment site within the apical region of the heart and temporarily and/or permanently affix the conduit to the upstream attachment site. As such, once the endovascular pathway is established, a first positioning magnet is delivered over the wire and under imaging to a selected location within the left ventricle thereby defining the upstream conduit attachment site. In one particular embodiment of the subject methods, by means of guidewires and/or guiding catheters, a first magnet is delivered under fluoroscopic imaging through a cut-down in the peripheral arterial system, such as in the femoral artery or the like, delivered into the aorta and made to cross the aortic valve into the left ventricle. Alternatively, the magnet may be delivered through the vena cava into the right atrium, through the atrial septal wall into the left atrium and across the mitral valve into the left ventricle. Using either pathway, the first magnet is selectively positioned against the internal wall of the left ventricle in the area of the apex and, once the most suitable position is determined, the first magnet is held in place. A second magnet, either independently or attached to the leading end of a conduit, is positioned externally over the apex and is allowed to be drawn by the magnetic force of the first magnet and be magnetically aligned with the first magnet. Where the magnets are annular or define a ring, the opening therein may be used to identify the upstream conduit attachment site.

A downstream conduit connection site on a wall of the descending aorta is also selected, and the descending aorta is then occluded at a location upstream of the selected site such as by an internal occlusion balloon. An internal vessel occlusion device, such as a balloon occlusion device, may be employed wherein an inflatable balloon is placed upstream of the target opening site. Optionally, a second inflatable balloon may be placed downstream of the selected opening site. As such, the balloon catheter system employed is configured to allow instruments to be delivered to a location between the two balloons and then laterally from there to the selected site on the wall of the descending aorta.

Once the balloons are inflated, a catheter puncturing means is then delivered to the target opening site and used to create an opening in the descending aorta at the selected location. The selected conduit is then prepared for delivery with its upstream end, which may have a second positioning magnet positioned thereon, in a leading position. The conduit is then delivered through the descending aorta through the opening and is brought into contact with the left ventricle such that the attached second magnet becomes self-aligned with the first magnet positioned within the left ventricle. While the magnets may serve solely as a guiding means and temporary fixation means for the conduits, they may also serve to permanently affix the conduit to the left ventricular wall. Still yet, other connectors, such as those disclosed in U.S. Pat. No. 5,676,670 and PCT International Publication No. WO 97/27898, may be used with or without the use of the aligning magnets to carry out the methods of the present invention.

Next, the downstream end of the conduit is attached to the opening created in the descending aorta. The downstream end may be attached by any of the means described above including suturing, stapling, clipping, etc. The downstream connection may also be formed by means of two oppositely polarized magnets where one magnet is attached about the opening in the descending aorta and the other is affixed to the downstream end of the conduit. Alternatively, other connectors such as those disclosed in the above cited publications may be employed.

A blood flow opening may now be established within the left ventricle at the conduit connection site. As with the direct surgical approach, the leakage of blood should be prevented. A sealing means such as those illustrated in FIGS. 5A, 5B, 6A and 6B may be used in a similar manner as used in the surgical approaches. Alternatively, a coring or puncturing catheter may be provided with a proximally situation occlusion member wherein the member is expanded or inflated within the conduit prior to creating the ventricular opening.

The one or more valves are positioned and attached at selected locations either within the conduit or within the descending aorta. Once the one or more valves are properly seated the sealing and/or occluding members may be removed from the conduit, the left ventricle and the descending aorta to allow blood flow through the conduit into the descending aorta.

In applications of the present invention involving the implantation of more than one conduits and/or valves, the conduits and/or valves may be implanted consecutively or concurrently with each other. Additionally, in applications of the present invention involving a regurgitant aortic valve, the surgical and endovascular procedures may further include permanently closing the aortic valve (such as by suturing together the leaflets), wherein all arterial blood from the left ventricle is directed through the one or more implanted conduits.

Kits of the Present Invention

Also provided by the subject invention are kits for use in practicing the subject methods. Certain of the kits of the subject invention include a selection or panel of conduits, those with integral valves or not, and a selection or panel of valves as described above. In other kits, various instruments are provided for performing the subject methods, where such additional instrumentation may include, but is not limited to, one or more guide wires, trocars, guide catheters, sealing device, occlusion catheters, etc. Finally, the kits may further include instructions for the direct, endoscopic and/or endovascular delivery and implantation of a conduit. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

It is evident from the above description and discussion that the above described invention provides devices and procedures by which the cardiac output function of heart can be improved. The above described invention provides a number of advantages, including the elimination of cardiopulmonary bypass and minimizing the number and size of incisions into the heart. Furthermore, the subject methods are easier to perform than conventional valve replacement and left ventricular remodeling procedures, and may reduce the risks, time and cost of the procedure. As such, the subject invention represents a significant contribution to the art.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Though the invention has been described in reference to certain examples, optionally incorporating various features, the invention is not to be limited to the embodiments described. It is to be understood that the breadth of the present invention is to be limited only by the literal or equitable scope of the following claims. That being said,

We claim:

1. A method comprising:
   providing a conduit having an upstream end and a downstream end; delivering the conduit to a location external to the heart between the left ventricle and the descending aorta;
   selecting a downstream conduit attachment site within the wall of the descending aorta;
   occluding blood flow through the descending aorta at the downstream conduit attachment site; forming an opening in the descending aorta at the downstream conduit attachment site;
   selecting an upstream conduit attachment site within the wall of the left ventricle; attaching the upstream end of the conduit to the upstream conduit attachment site; accessing the upstream attachment site through the conduit;
   and forming an upstream opening in the left ventricular wall at the upstream conduit attachment site.

2. The method of claim 1 further comprising preventing the escape of blood from the open upstream attachment site while forming the upstream opening therein.

3. The method of claim 2, wherein the preventing the escape of blood comprises sealing the upstream opening from inside the left ventricle.

4. The method of claim 3, wherein the sealing comprises inflating a balloon.

5. The method of claim 3, wherein the sealing comprises expanding a mesh.

6. The method of claim 2, wherein the preventing comprises occluding the conduit adjacent the upstream opening.

7. The method of claim 1, wherein the accessing the upstream attachment site through the conduit comprises accessing the conduit through the downstream end of the conduit.

8. The method of claim 1, wherein the accessing the upstream attachment site through the conduit comprises accessing the conduit through a port within a side wall of the conduit.

9. The method of claim 1, further comprising inserting a valve into the conduit.

10. The method of claim 1, further comprising implanting a valve within the descending aorta.

11. The method of claim 1, wherein the occluding blood flow through the descending aorta comprises inflating at least one balloon within the descending aorta.

* * * * *